(12) United States Patent
Frayer et al.

(10) Patent No.: US 9,995,627 B2
(45) Date of Patent: Jun. 12, 2018

(54) RASTER OPTIC DEVICE FOR OPTICAL HYPER SPECTRAL SCANNING

(71) Applicant: Smiths Detection Inc., Edgewood, MD (US)

(72) Inventors: Maxim Frayer, Sherman, CT (US); Juan Ivaldi, Danbury, CT (US); Peng Zou, Ridgefield, CT (US)

(73) Assignee: SMITHS DETECTION INC., Edgewood, MD (US)

( * ) Notice: Subject to any disclaimer, the term of this patent is extended or adjusted under 35 U.S.C. 154(b) by 63 days.

(21) Appl. No.: 14/447,811

(22) Filed: Jul. 31, 2014

(65) Prior Publication Data
US 2016/0033393 A1    Feb. 4, 2016

(51) Int. Cl.
| G01J 3/46 | (2006.01) |
| G01J 3/28 | (2006.01) |
| G01J 3/02 | (2006.01) |
| G01N 21/65 | (2006.01) |

(52) U.S. Cl.
CPC .............. *G01J 3/2823* (2013.01); *G01J 3/021* (2013.01); *G01J 3/0202* (2013.01); *G01J 3/0208* (2013.01); *G01J 3/0237* (2013.01); *G01J 3/0272* (2013.01); *G01J 2003/2826* (2013.01); *G01N 21/65* (2013.01); *G01N 2201/10* (2013.01)

(58) Field of Classification Search
CPC .... G01J 3/2823; G01N 21/65; G01N 2201/10
USPC ........................................................ 356/402
See application file for complete search history.

(56) References Cited

U.S. PATENT DOCUMENTS

| 5,233,352 A * | 8/1993 | Cournane ............. G01S 13/325 342/124 |
| 5,982,484 A * | 11/1999 | Clarke ...................... G01J 3/44 356/301 |
| 7,633,048 B2 | 12/2009 | Doran et al. |
| 2003/0226977 A1 | 12/2003 | Storz et al. |
| 2004/0090621 A1 | 5/2004 | Bennett et al. |
| 2004/0127778 A1* | 7/2004 | Lambert ............ A61B 5/14532 600/318 |
| 2004/0135235 A1* | 7/2004 | Poveda ................... H01L 21/84 257/656 |

(Continued)

FOREIGN PATENT DOCUMENTS

| EP | 1019773 B1 | 7/2000 |
| WO | 0008512 | 2/2000 |

OTHER PUBLICATIONS

Search Report dated Nov. 11, 2015 in Application # PCT/US2015/042919.

(Continued)

*Primary Examiner* — Hina F Ayub
(74) *Attorney, Agent, or Firm* — Kevin E. West; Advent, LLP

(57) ABSTRACT

A spectroscopic scanning device, a portable spectroscopic scanning system, and methods for using the spectroscopic scanning device are described that include at least one focusing element configured to collect light, a beam-steering element configured to direct a portion of the collected light from the at least one focusing element, and a detector configured to receive the directed light from the beam-steering element, wherein the beam-steering element is operable to successively select portions of light from a plurality of locations within its field of regard.

19 Claims, 4 Drawing Sheets

(56) References Cited

U.S. PATENT DOCUMENTS

| | | | | |
|---|---|---|---|---|
| 2005/0003862 A1* | 1/2005 | Johnson | ............... | H01Q 1/125 455/561 |
| 2008/0147051 A1 | 6/2008 | Kessler et al. | | |
| 2008/0251720 A1* | 10/2008 | Xu | ..................... | G01B 11/24 250/332 |
| 2011/0080580 A1* | 4/2011 | Fermann | ............... | G01N 21/31 356/301 |
| 2011/0205527 A1 | 8/2011 | Prater et al. | | |
| 2012/0092650 A1* | 4/2012 | Gunn, III | ........... | G01N 21/7746 356/73 |
| 2013/0162990 A1* | 6/2013 | Kobayashi | .............. | G01J 3/021 356/301 |
| 2014/0132957 A1* | 5/2014 | Messerschmidt | .... | A61B 5/0075 356/409 |
| 2014/0149811 A1* | 5/2014 | Ross | ................... | G01R 31/311 714/724 |
| 2014/0160476 A1* | 6/2014 | Goyal | ................... | G01N 21/55 356/402 |
| 2015/0062320 A1* | 3/2015 | Tunnell | ............... | A61B 5/0075 348/77 |

OTHER PUBLICATIONS

International Preliminary Report on Patentability dated Feb. 9, 2017 for International Appln. No. PCT/US2015/042919.
Extended European Search Report dated Feb. 26, 2018 for European Appln. No. 15827573.5.

* cited by examiner

RASTER OPTIC DEVICE FOR OPTICAL HYPER SPECTRAL SCANNING

BACKGROUND

Generally, infrared (IR) spectroscopy is based on molecular vibration and rotation modes, as well as combination and overtone bands. Because molar absorptivity in the near-infrared (NIR) region of the electromagnetic spectrum can be quite small, NIR radiation can typically penetrate quite far into a sample (e.g., as compared to mid-infrared (MIR) radiation). Thus, IR spectroscopy techniques, such as diffuse reflectance NIR spectroscopy, can be useful for probing bulk material. Further, NIR spectroscopy generally requires limited or no sample preparation. Near-infrared spectroscopy (NIRS) can be used in materials characterization and molecular analysis applications as diverse as pharmaceuticals, medical diagnostics, neurology, neuroimaging, neonatal research, urology, food and agrochemical quality control, combustion product analysis, sports medicine, sports science, sports training, ergonomics, rehabilitation, and so forth.

Raman spectroscopy, another form of vibrational spectroscopy, can be used to determine vibrational, rotational, and/or other vibrational modes of a sample and/or sample components. Generally, Raman spectroscopy uses inelastic scattering (e.g., Stokes and Anti-Stokes scattering) of monochromatic light, which can be furnished using, for instance, a laser in the visible, NIR, or ultraviolet range. The laser light interacts with a sample, which shifts the energy of photons scattered by the sample from the laser. The energy shift can provide information about vibrational modes of the molecules that constitute the sample. Frequencies of molecular vibrations are specific to the chemical bonds and symmetry of molecules; thus the vibrational spectrum can be used to identify a particular sample and/or sample components. With Raman spectroscopy, little or no sample preparation is required. Further, Raman spectra can be collected from small volume samples (e.g., measuring less than approximately one micrometer (1 µm) in diameter). Raman spectroscopy can also be used in diverse applications including pharmaceuticals, medicine, chemistry, physics, nanotechnology, and so forth.

SUMMARY

A spectroscopic scanning device, a portable spectroscopic scanning system, and methods for using the spectroscopic scanning device are described that include at least one focusing element configured to collect light, a beam-steering element configured to direct a portion of the collected light from the at least one focusing element, and a detector configured to receive the directed light from the beam-steering element, wherein the beam-steering element is operable to successively select portions of light from a plurality of locations within its field of regard. Additionally, a portable spectroscopic scanning system can include a laser source; a beam splitter configured to direct a laser beam from the laser source; a beam-steering element configured to direct a portion of the laser beam and collected light from the at least one focusing element; at least one focusing element configured to collect light; a detector configured to receive the directed light from at least one of the beam-steering element or the beam splitter; and control circuitry coupled to at least one of the laser source or the detector; wherein the beam-steering element is operable to successively select portions of light from a plurality of locations within its field of regard. In an implementation, a process for utilizing the spectroscopic scanning device that employs the techniques of the present disclosure includes initiating illumination of a sample with electromagnetic radiation using at least one of a laser source or control circuitry, and receiving an indication of at least one of a presence or an absence of a constituent of the sample determined by detecting a sample constituent of a sample by analyzing a characteristic of electromagnetic radiation obtained from the sample associated with the laser source using a portable spectroscopic scanning device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

DETAILED DESCRIPTION

Spectroscopy systems can include an IR spectroscopy system, a Raman spectroscopy system, and/or other spectroscopy systems. For diffuse reflectance and scattering spectroscopy, it is occasionally necessary to raster the output beam at the sample focal plane. One purpose for rastering the output beam can include preventing combustion or thermal activation of the sample, either for non-destructive testing or for preventing a dangerous reaction of an active material. The temporal frequency of a raster drive can be directly proportional to the average energy absorbed (and then dissipated) by the sample due to the high source intensity. Another purpose for rastering an output beam can include scanning a larger effective area of the sample plane than may be scanned by the native footprint of an optical probe for locating a heterogeneous component of interest and/or insuring more exhaustive coverage of the sample plane, for example. However, using a spectroscopy system for these purposes and utilizing raster scanning requires a system with large components that make it difficult to utilize in portable systems.

Accordingly, a spectroscopic scanning device, a portable spectroscopic scanning system, and methods for using the spectroscopic scanning device are described that include at least one focusing element configured to collect light, a beam-steering element configured to direct a portion of the collected light from the at least one focusing element, and a detector configured to receive the directed light from the beam-steering element, wherein the beam-steering element is operable to successively select portions of light from a plurality of locations within its field of regard. Additionally, a portable spectroscopic scanning system can include a laser source; a beam splitter configured to direct a laser beam from the laser source; a beam-steering element configured to direct a portion of the laser beam and collected light from the at least one focusing element; at least one focusing element configured to collect light; a detector configured to receive the directed light from at least one of the beam-steering element or the beam splitter; and control circuitry coupled to at least one of the laser source or the detector; wherein the beam-steering element is operable to successively select portions of light from a plurality of locations within its field of regard. In an implementation, a process for utilizing the spectroscopic scanning device that employs the techniques of the present disclosure includes initiating illumination of a sample with electromagnetic radiation using at least one of a laser source or control circuitry, and receiving an indication of at least one of a presence or an absence of a constituent of the sample determined by detecting a sample constituent of a sample by analyzing a characteristic of electromagnetic radiation obtained from the sample associated with the laser source using a portable spectroscopic scanning device.

Figure 1:
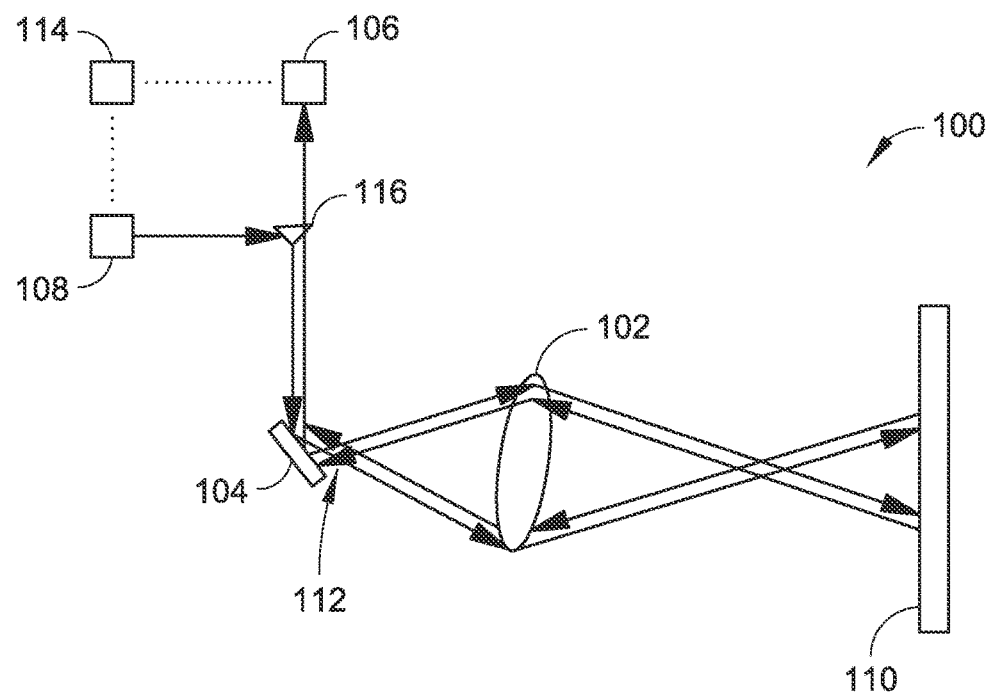
FIG. 1 is a diagrammatic view illustrating a spectroscopic scanning device that includes a beam-steering element operable to successively select portions of light from a plurality of locations within its field of regard in accordance with an example implementation of the present disclosure.

Spectroscopy systems in accordance with the present disclosure can provide improved optical spectrometer detection performance using, for example, a beam steering element configured to be used with scanning capability, where the beam steering element has multiple degrees of freedom instead of one degree of freedom. Additionally, this provides for a smaller system that can be used in a portable device or a handheld instrument for quickly detecting and/or identifying a broad range of substances (e.g., chemicals on a sample). This results in a smaller device with fewer parts, reduced size, reduced weight, and reduced power consumption FIG. 1 illustrates a spectroscopic scanning device 100 in accordance with example implementations of the present disclosure. As shown, the spectroscopic scanning device 100 includes a laser source 108. In implementations, the laser source 108 may include a light source configured to provide different types of light. In one embodiment, the laser source 108 can be configured to provide infrared (IR) light. In some implementations, an IR source can include a broadband source of, for example, NIR radiation, such as a tungsten vacuum light source (e.g., a tungsten lamp), an incandescent light bulb, a quartz halogen light bulb, a light-emitting diode (LED), and so forth. In a specific example, a laser source 108 can include a tungsten vacuum source. In some instances, multiple sources of IR radiation can be included with an IR source, and a particular source of IR radiation can be selected based upon a specific sample or group of samples.

In another embodiment, the laser source 108 can be configured to include a Raman excitation light source. A Raman excitation light source can include a source of at least substantially monochromatic light, such as an excitation laser, having a substantially greater irradiance (e.g., amount of electromagnetic radiation per unit area) than the IR source. In some embodiment, the light source can include a diode laser, a gas laser, a crystal laser, and so forth. In a specific example, a laser source 108 includes a focused diode laser. In some implementations, the excitation laser can be a polarized excitation laser. In implementations, the light source can be implemented using a coaxial laser with a prism (e.g., beam splitter 116 and/or a lens) configured to focus the laser light onto a sample plane and/or sample target 110. However, a coaxial laser is provided by way of example only and is not meant to be restrictive of the present disclosure. In other implementations, the light source can be implemented as a non-coaxial laser. Further, the light source can be implemented using a light shield. For example, a CCD array detector can be shielded from a laser path of a light source. In embodiments, the laser source 108 can include other diode laser sources.

The laser source 108 can furnish light having various characteristics. For example, different laser wavelengths can be selectively used to illuminate a sample target 110. In some instances, multiple lasers (e.g., configured as a laser array) having various wavelengths can be included with the laser source 108, and a particular laser or wavelength can be selected based upon a specific sample or group of samples. In a specific embodiment, a laser wavelength can be determined that is suited for a particular sample or sample type, and that laser wavelength can be selectively activated and/or initiated.

As shown in FIG. 1, the spectroscopic scanning device 100 can include a beam splitter 116. In implementations, beam splitter 116 can include an optical device for splitting a beam of light into multiple parts. In one specific embodiment, a beam splitter 116 includes a prism that is configured to direct a beam of light from laser source 108 to a beam-steering element 104 and to a sample target 110. Additionally, beam splitter 116 can be configured to direct a beam of light from a beam-steering element 104 to a detector 106 and/or other device. In some implementations, beam splitter 116 can include a beam divider, such as a dichroic beam splitter, a spatially coated beam splitter, a partial mirror, and so forth. Additional examples of a beam splitter 116 can include a cube including two triangular prisms, a half silvered mirror, a metallic coating, etc. In one specific implementation, beam splitter 116 can include a plate oriented at a forty-five degree (45°) angle with respect to a laser source 108 and/or a beam-steering element 104 where a first Raman signal is at least substantially reflected from the beam divider plate and a second light signal reflected from a sample target 110 is transmitted through the beam splitter 116 in a direction different from the first Raman signal. This can allow for simultaneous operation of reflecting/transmitting a first light beam and reflecting/transmitting a second light beam. Other beam splitter 116 configurations can also be used, including aperture splitting and/or other spatial beamsplitting techniques.

Figure 2:
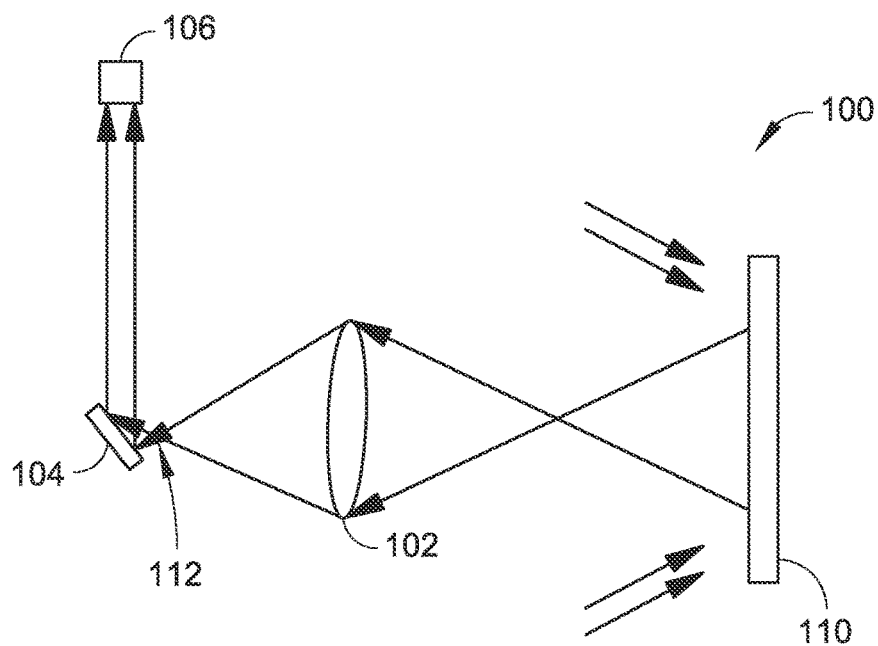
FIG. 2 is a diagrammatic view illustrating a spectroscopic scanning device that includes a beam-steering element operable to successively select portions of light from a plurality of locations within its field of regard in accordance with an example implementation of the present disclosure.
Figure 3:
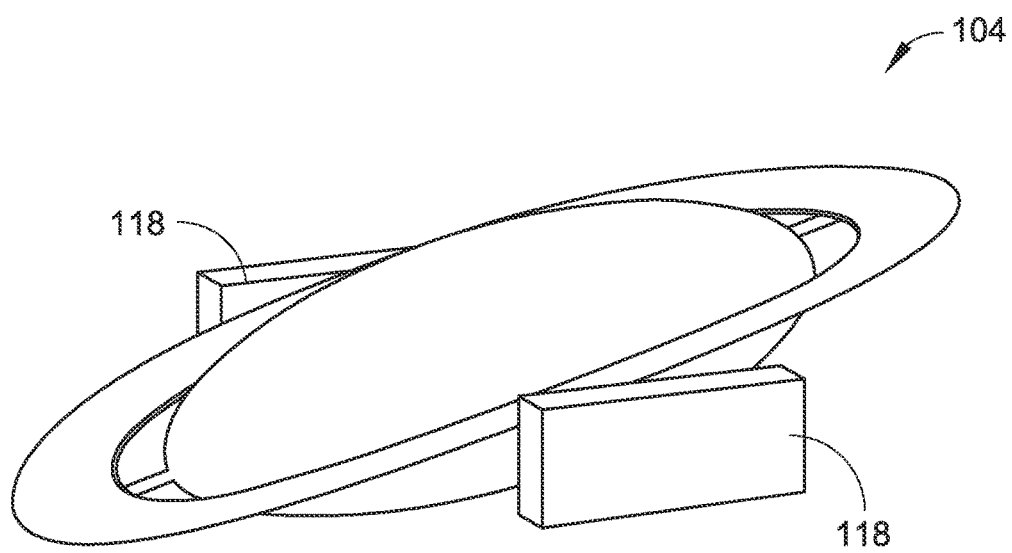
FIG. 3 is a diagrammatic view illustrating a beam-steering element operable to successively select portions of light from a plurality of locations within its field of regard in accordance with an example implementation of the present disclosure.

As shown in FIGS. 1 through 3, the spectroscopic scanning device 100 includes a beam-steering element 104. In implementations, a beam steering element 104 can include an element configured to direct a light beam, where the beam steering element 104 can be reflective and/or transmissive. Additionally, the beam steering-element 104 can be operable to successively select portions of light from a plurality of locations within its field of regard (e.g., focus area 120), such as when using a raster scanning configuration. In one implementation, the beam steering element 104 can include a microelectromechanical (MEMS) scanning mirror, such as the MEMS scanning mirror shown in FIG. 3. In this implementation, the MEMS scanning mirror can include at least one actuator assembly 118 (e.g., a motor for moving/controlling the MEMS mirror) configured to adjust the position of the MEMS mirror. In some embodiments, a MEMS mirror can have a diameter from about 1 mm to about 10 mm. In embodiments, the actuator assembly 118 can provide multiple degrees of freedom for the beam steering element 104. This multiple degree-of-freedom capability can be especially beneficial when the spectroscopic scanning device 100 is used for raster scanning. The actuator assembly 118 may include a conventional actuator mechanism or a MEMS type actuator configured for rapid scanning frequency. In a specific example, a beam steering element 104 can include a MEMS mirror having a pure silicon component that employs magnetic actuation using an electrical current flowing on a mirror coil under a magnetic field, which in turn induces displacement of the reflective area (e.g., the MEMS mirror). In implementations, the actuator assembly 118 can be programmed to adjust the beam steering element 104 in a desired raster scan pattern. Additionally, the actuator assembly 118 can be communicatively coupled to control circuitry 114 such that control circuitry 118 can transmit instructions to the actuator assembly 118. In one specific implementation, the actuator assembly 118 and the beam steering element 104 can be configured to perform a static scan (e.g., the focus area 120 does not substantially change location). In another specific implementation, the actuator assembly 118 and the beam steering element 104 can be configured to perform a fast scan (e.g., the focus area 120 changes rapidly in order to cover a greater area).

Figure 4:
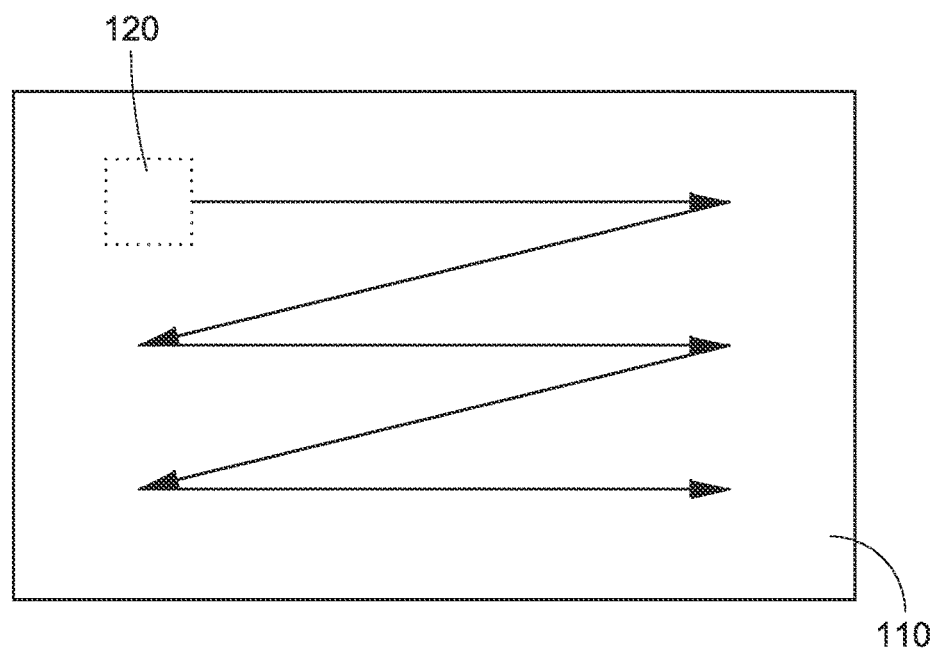
FIG. 4 is a diagrammatic view illustrating a raster scanning pattern in accordance with an example implementation of the present disclosure.

In an example and as shown in FIG. 1, a beam steering element 104 that includes a MEMS mirror with an actuator assembly 118 can reflect/transmit a first beam of light to a sample target 110 from a beam splitter 116 and laser source 108 in a raster scanning configuration (e.g., the focus area 120 on the target sample 110 can be scanned in a rectangular pattern, as shown in FIG. 4, and/or a circular pattern, a spiral pattern, etc.). In this example, the beam steering element 104 can simultaneously reflect/transmit a second beam of light reflected from the sample target 110 along the same path as the first beam of light to the beam splitter 116 and a detector 106. In implementations, a focal point 112 of the first light beam and/or the second light beam can be disposed proximate but not on the beam-steering element 104 and between the beam-steering element 104 and the focusing element 102. This allows a smaller beam-steering element 104 and provides for a smaller spectroscopic scanning device.

As shown in FIGS. 1 and 2, the spectroscopic scanning device 100 includes a focusing element 102. In implementations, the focusing element 102 can include a lens configured for focusing and/or directing the first beam of light and the second beam of light to and from the sample target 110. A lens may include an optical device that transmits and refracts light either converging or diffracting the beam. For example, the focusing element 102 can include a telescopic lens, which may be configured to be adjustable (e.g., the telescopic lens may be adjustable in order to change position of a focal point and/or may be adjusted to move a light beam in a plane perpendicular to the direction of the light beam). In an additional embodiment, the focusing element 102 can include a simple lens. In implementations, the focusing element 102 may be disposed between the beam steering element 104 and the sample target 110. In embodiments, the focusing element 102 can be moved and/or adjusted closer to or farther from the beam-steering element 104 and/or moved off-axis from the light transmitted between the beam-steering element 104 and the sample target 110.

As shown in FIGS. 1 and 2, the spectroscopic scanning device 100 includes a detector 106. In implementations, the detector 106 can include an IR detector configured to detect infrared light. The IR detector can include one or more detector components, which can be selected based upon a range of electromagnetic wavelengths to be measured. For example, the IR detector can include an indium gallium arsenide (InGaAs) detector array, a lead(II) sulfide (PbS) detector array, a silicon-based charge-coupled device (CCD), and so forth. In some instances, a two-dimensional (2D) array detector using an acousto-optic tunable filter can be used to record multiple images sequentially at different narrow wavelength bands. In other implementations, the detector 106 can include a Raman detector configured to detect Raman energy. The Raman detector can comprise one or more detector components including a charge-coupled device (CCD), a photomultiplier tube (PMT), a photodiode, and so forth. In instances where the light source 108 comprises a polarized excitation laser, the Raman detector can be implemented using a polarization analyzer, which can acquire spectra at multiple orientations (e.g., both perpendicular and parallel) with respect to the excitation plane of the light source 108. The spectra can be used to calculate a depolarization ratio, which can be used to determine symmetry, Raman activity, and/or peaks in the spectra.

In some implementations, detector 108 can include multiple detectors. In one instance, both silicon-based CCD detectors and InGaAs detectors can be employed. In these configurations, UV, visible, and NIR spectra can be recorded together. Further, a spectroscopic scanning device 100 configured for one range of electromagnetic wavelengths may also be used for another range of wavelengths. For instance, the range of an MIR instrument may extend at least partially into the NIR. Thus, in some instances, a single IR detection component can be used for both NIR and MIR. In other implementations, a spectroscopic scanning device 100 configured for UV and/or visible light may be capable of recording spectra in at least a portion of the NIR range. Thus, an IR detector 106 may comprise one or more UV and/or visible light detectors.

In a specific embodiment illustrated in FIG. 2, spectroscopic scanning device 100 includes a detector 106, a focusing element 102, and a beam-steering element 104 operable to successively select portions of light from a plurality of locations within its field of regard. In this embodiment, ambient light reflects from a sample target 110 and into the spectroscopic scanning device 100. The focal point 112 of the ambient light reflected from the sample target 110 and through the focusing element 102 to the beam-steering element 104 is disposed proximate to but not on the beam-steering element 104.

Figure 5:
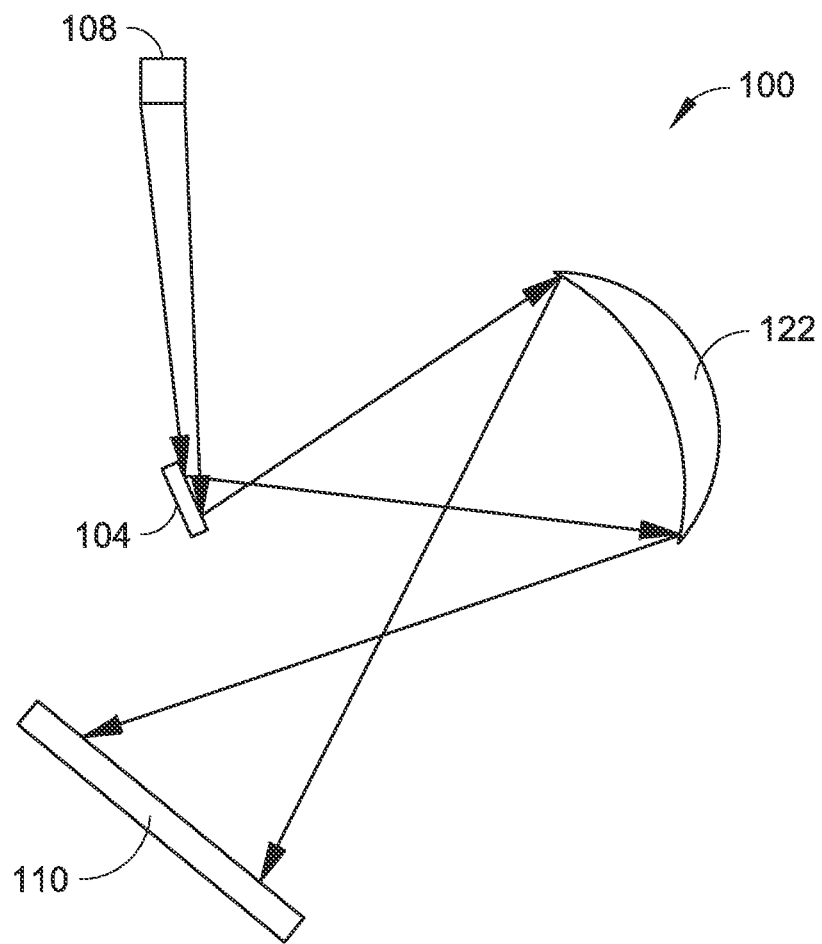
FIG. 5 is a diagrammatic view illustrating a spectroscopic scanning device that includes a beam-steering element operable to successively select portions of light from a plurality of locations within its field of regard in accordance with an example implementation of the present disclosure.

In an additional embodiment illustrated in FIG. 5, the spectroscopic scanning device 100 may include a curved mirror element 122. In some implementations, a curved mirror element 122 can include a concave or otherwise curved device configured for reflecting/transmitting light along a path. In one specific embodiment, the curved mirror element 122 can include a concave mirror configured to be reflect and transmit a beam of light in the spectroscopic scanning device 100.

As illustrated in FIGS. 1 and 2, the spectroscopic scanning device 100 can include control circuitry 114. For example, the detector 106 and/or laser source 108 may be coupled with a control circuitry 114 for controlling the detector 106 and/or laser source 108. The control circuitry 114 may include a processing module, a communications module, and/or a memory module. The processing module provides processing functionality for the control circuitry 114 and may include any number of processors, microcontrollers, or other processing systems and resident or external memory for storing data and other information accessed or generated by the control circuitry 114. The processing module may execute one or more software programs, which implement techniques described herein. The processing module is not limited by the materials from which it is formed or the processing mechanisms employed therein, and as such, may be implemented via semiconductor (s) and/or transistors (e.g., using electronic integrated circuit (IC) components), and so forth. The communications module is operatively configured to communicate with components of the detector 106 and/or laser source 108. The communications module is also communicatively coupled with the processing module (e.g., for communicating inputs from the detector 106 and/or laser source 108 to the processing module). The communications module and/or the processing module can also be configured to communicate with a variety of different networks, including the Internet, a cellular telephone network, a local area network (LAN), a wide area network (WAN), a wireless network, a public telephone network, and/or an intranet, for example.

The memory module is an example of tangible computer-readable media that provides storage functionality to store various data associated with operation of the control circuitry 114, such as software programs and/or code segments, or other data to instruct the processing module and possibly other components of the control circuitry 114 to perform the steps described herein. Thus, the memory can store data, such as a program of instructions for operating a spectroscopy system (including its components), data, and so on. Although a single memory module is described, a wide variety of types and combinations of memory (e.g., tangible memory, non-transitory) may be employed. The memory module may be integral with the processing module, may comprise stand-alone memory, or may be a combination of both.

The memory module may include removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the detector 106 and/or laser source 108 and/or memory module may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

Figure 6:
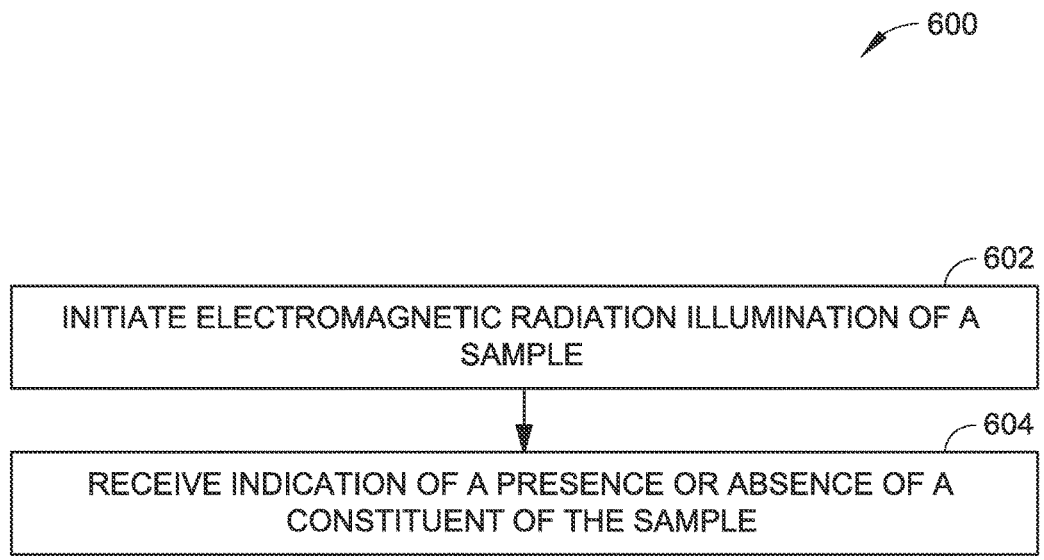
FIG. 6 is a flow diagram illustrating an example process for utilizing the spectroscopic scanning device illustrated in FIGS. 1 through 5.

FIG. 6 illustrates an example process 600 that employs the disclosed techniques to employ a spectroscopic scanning device, such as the spectroscopic scanning device 100 shown in FIGS. 1 through 5.

Accordingly, electromagnetic radiation illumination of a sample is initiated (Block 602). In implementations, control circuitry 114 can cause laser source 108 to initiate electromagnetic radiation in the form of a first light beam (e.g., a laser) configured to illuminate a sample target 110. In one example, the first light beam can be infrared radiation. In another example, the first light beam can be Raman radiation. In some instances, control circuitry can include a user interface, where a user can enter an initiation command.

Next, an indication of a presence or an absence of a constituent of a sample is received (Block 604). In implementations, the first light beam can be transmitted from a laser source 108 to a sample target 110. In this implementation, the first light beam can pass through and/or be directed by other devices (e.g., beam splitter 116, beam-steering element 104, focusing element 102, etc.). Light reflected from the sample target 110 can include a second beam of light, which is reflected along substantially the reverse path of the first beam of light to detector 106. Detector 106 can detect and/or analyze the second beam of light using control circuitry 114 to determine whether a predetermined sample constituent is present in/on the sample target 110 using the second beam of light.

Although the invention has been described in language specific to structural features and/or methodological acts, it is to be understood that the invention defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claimed invention.

What is claimed is:

1. A spectroscopic scanning device, comprising:
at least one lens configured to collect light;
a beam-steering element that is at least one of reflective or transmissive, the beam-steering element directing a portion of the collected light from the at least one lens, the beam-steering element having multiple degrees of freedom, wherein a focal point of the collected light is disposed proximate to the beam-steering element and between the beam-steering element and the at least one lens;
a detector configured to receive the directed light from the beam-steering element,
wherein the beam-steering element is operable to successively select portions of light from a plurality of locations within its field of regard; and
control circuitry configured to analyze a characteristic of the directed light and to indicate at least one of a presence or an absence of a constituent of a sample associated with the directed light.

2. The spectroscopic scanning device of claim 1, wherein the at least one lens includes two or more lenses.

3. The spectroscopic scanning device of claim 1, wherein the at least one lens is configured to be reflective.

4. The spectroscopic scanning device of claim 1, wherein the beam-steering element includes two degrees of freedom.

5. The spectroscopic scanning device of claim 1, wherein the beam-steering element is configured to perform progressive sequential scanning.

6. The spectroscopic scanning device of claim 1, wherein the beam-steering element is configured to perform random scanning.

7. The spectroscopic scanning device of claim 1, wherein the beam-steering element is configured to perform progressive sequential scanning and subsequently perform random scanning.

8. The spectroscopic scanning device of claim 1, wherein the beam-steering element includes a focusing element.

9. The spectroscopic scanning device of claim 1, wherein the beam-steering element includes a mirror.

10. The spectroscopic scanning device of claim 1, wherein the detector includes at least one of a photomultiplier or a diode or a detector array.

11. The spectroscopic scanning device of claim 1, further comprising a laser source.

12. The spectroscopic scanning device of claim 1, wherein the at least one lens is configured to collect light from a Raman excitation light source.

13. The spectroscopic scanning device of claim 1, wherein the beam-steering element includes a mirror.

14. The spectroscopic scanning device of claim 1, wherein the detector is a Raman detector.

15. A portable spectroscopic scanning system, comprising:
   a laser source;
   a beam splitter configured to direct a laser beam from the laser source;
   a beam-steering element that is at least one of reflective or transmissive, the beam-steering element directing a portion of the laser beam and collected light from at least one lens, the at least one lens configured to collect light, the beam-steering element having multiple degrees of freedom, wherein a focal point of the collected light is disposed proximate to the beam-steering element and between the beam-steering element and the at least one lens;
   a detector configured to receive the directed light from at least one of the beam-steering element or the beam splitter; and
   control circuitry coupled to the detector, the control circuitry configured to analyze a characteristic of the directed light and to indicate at least one of a presence or an absence of a constituent of a sample associated with the directed light,
   wherein the beam-steering element is operable to successively select portions of light from a plurality of locations within its field of regard.

16. The portable spectroscopic scanning system of claim 15, wherein the laser source includes an infrared laser source.

17. The portable spectroscopic scanning system of claim 15, wherein the laser source includes a Raman excitation laser.

18. The portable spectroscopic scanning system of claim 15, wherein the beam-steering element is configured to perform a raster scan of a sample target.

19. A method, comprising:
   initiating illumination of a sample with electromagnetic radiation using at least one of a laser source or control circuitry;
   receiving an indication of at least one of a presence or an absence of a constituent of the sample determined by detecting a sample constituent of the sample by analyzing a characteristic of electromagnetic radiation obtained from the sample associated with the laser source using a portable spectroscopic scanning device that includes
   at least one lens configured to collect light;
   a beam-steering element that is at least one of reflective or transmissive, the beam-steering element directing a portion of the collected light from the at least one lens, the beam-steering element having multiple degrees of freedom, wherein a focal point of the collected light is disposed proximate to the beam-steering element and between the beam-steering element and the at least one lens,
   a Raman detector configured to receive the directed light from the beam-steering element; and
   control circuitry configured to analyze a characteristic of the directed light and to indicate at least one of a presence or an absence of a constituent of a sample associated with the directed light,
   wherein the beam-steering element is operable to successively select portions of light from a plurality of locations within its field of regard.

\* \* \* \* \*